US012680113B2

(12) United States Patent
Shkolnikov et al.

(10) Patent No.: US 12,680,113 B2
(45) Date of Patent: Jul. 14, 2026

(54) SINGLE CELL TRANSFECTION WITH INTERCHANGEABLE REAGENT

(71) Applicant: Hewlett-Packard Development Company, L.P., Spring, TX (US)

(72) Inventors: Viktor Shkolnikov, Palo Alto, CA (US); Alexander Govyadinov, Corvallis, OR (US)

(73) Assignee: HEWLETT-PACKARD DEVELOPMENT COMPANY, L.P., Spring, TX (US)

( * ) Notice: Subject to any disclaimer, the term of this patent is extended or adjusted under 35 U.S.C. 154(b) by 881 days.

(21) Appl. No.: 17/429,962

(22) PCT Filed: Jun. 24, 2019

(86) PCT No.: PCT/US2019/038737
§ 371 (c)(1),
(2) Date: Aug. 11, 2021

(87) PCT Pub. No.: WO2020/263218
PCT Pub. Date: Dec. 30, 2020

(65) Prior Publication Data
US 2022/0145331 A1      May 12, 2022

(51) Int. Cl.
*C12N 15/87*      (2006.01)
*B01L 3/00*      (2006.01)
*C12M 1/42*      (2006.01)

(52) U.S. Cl.
CPC ........ *C12N 15/87* (2013.01); *B01L 3/502761* (2013.01); *C12M 35/02* (2013.01); *C12M 35/04* (2013.01); *B01L 2200/0647* (2013.01)

(58) Field of Classification Search
None
See application file for complete search history.

(56) References Cited

U.S. PATENT DOCUMENTS

2005/0260745 A1* 11/2005 Domansky .......... B01L 3/50255
435/294.1
2008/0044894 A1* 2/2008 Lee ........................ C12M 23/16
435/307.1
(Continued)

FOREIGN PATENT DOCUMENTS

CN      107988070 A      5/2018
CN      108368522 A      8/2018
(Continued)

OTHER PUBLICATIONS

Chang, et al., Magnetic Tweezers-based 3D Microchannel Electropora-tion for High-Throughput Gene Transfection in Living Cells, Apr. 15, 2015, HHS Public Access, Small, 20 pages.
(Continued)

*Primary Examiner* — Michael A Marcheschi
*Assistant Examiner* — Ashley Lopezlira
(74) *Attorney, Agent, or Firm* — FOLEY & LARDNER LLP

(57) ABSTRACT

A device, method, and system can perform single cell transfection using a transfection chamber on a transfection chip. The system may include a fluidic channel located on the transfection chip for guiding a cell towards the trans-fection chamber, the fluidic channel sized to allow no more than a single cell to arrive at the transfection chamber at a time. The system may also include a reagent receiver located on the transfection chip guiding received reagent towards the transfection chamber and intersecting with the path of the fluidic channel.

6 Claims, 13 Drawing Sheets

(56) References Cited

U.S. PATENT DOCUMENTS

| | | | |
|---|---|---|---|
| 2011/0213288 | A1 | 9/2011 | Choi et al. |
| 2014/0256047 | A1 | 9/2014 | Lee et al. |
| 2015/0197720 | A1 | 7/2015 | Chiou et al. |
| 2017/0246867 | A1* | 8/2017 | Govyadinov ........ B41J 2/04581 |
| 2018/0029032 | A1* | 2/2018 | Govyadinov ....... B01L 3/50273 |
| 2020/0048599 | A1* | 2/2020 | Firouzi ................... B01J 19/08 |
| 2020/0123484 | A1* | 4/2020 | Tseng ..................... C12M 23/16 |

FOREIGN PATENT DOCUMENTS

| | | | | |
|---|---|---|---|---|
| CN | 108531396 | A | 9/2018 | |
| WO | WO-2008100749 | A2 | 8/2008 | |
| WO | WO-2018013135 | A1 * | 1/2018 | ............ B01D 35/26 |
| WO | WO-2018039084 | A1 | 3/2018 | |
| WO | WO-2019068022 | A1 | 4/2019 | |
| WO | WO-2019079787 | A1 | 4/2019 | |

OTHER PUBLICATIONS

Chow, et al., Single Cell Transfection through Precise Microinjection with Quantitatively Controlled Injection Volumes, Apr. 12, 2016, Scientific Reports, Jan. 2016, 9 pages.

* cited by examiner

<u>100</u>

200

300

400

500

600

700

800

900

1000

1100

1200

1302

1304

1300

SINGLE CELL TRANSFECTION WITH INTERCHANGEABLE REAGENT

This application is a national stage application under 35 U.S.C. 371 of PCT Application PCT/US2019/038737, filed Jun. 24, 2019; said application incorporated herein by reference.

BACKGROUND

Transfection is the process of deliberately introducing naked or purified nucleic acids into cells. Transfection can be accomplished by poration, which is the opening of temporary pores in a cell membrane to allow a reagent such as nucleic to across the cell membrane and into a cell. Poration may be performed by an electrical pulse or other physical or chemical means.

DESCRIPTION OF THE DRAWINGS

Certain examples are described in the following detailed description and in reference to the drawings, in which.

DETAILED DESCRIPTION

This present disclosure relates to a method, device, and system in single cell transfection. Transfection can be accomplished by poration which is the formation of temporary pores or holes in the surface of the cell. The disclosed system further enables single cell level automated electrotransfection with single and simultaneously multiple and combinatorically assembled sets of reagents.

An example system includes a reagent dispenser, a cell transfection chip with microorifices or fluidic channels to receive the reagents, a transfection inducing chamber, and an outlet. The transfection may be achieved by electrical, physical, or chemical means. The outlet may be to an internal storage or to a manipulation chamber, or to an ejector to eject the cells into a multiwell plate on a computer controlled stage.

The system enables the combinatorial probing of cells with various reagents to selectively modulate various signaling pathways across the cell. For example, this can include introduction of various regulatory RNAs or other combinatorial genetic modification of the cell such as via CRISPR like process with differing guide RNAs.

The ability to accomplish precision transfection, referred to here as transfection on a single cell level enables a wide variety of cell biological studies. Similarly, the ability to perform combinatorial transfection is enabled by this single cell transfection as the transfection of a specifically controlled material can be done on a cell by cell basis.

Figure 1:
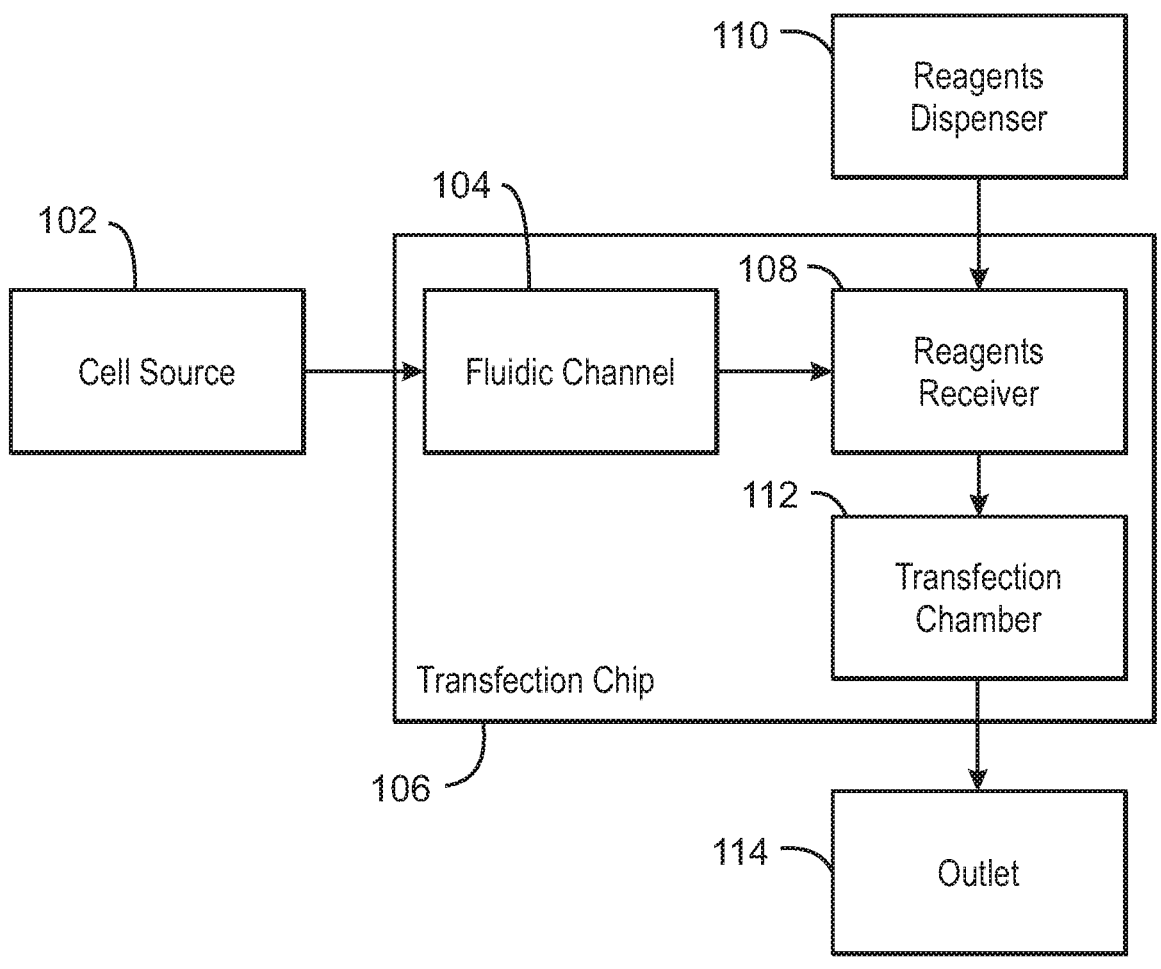
FIG. 1 is a block diagram of a single cell transfection chip, in accordance with an example.

FIG. 1 is a block diagram of a single cell transfection chip system 100, in accordance with an example. As described herein, transfection refers to the process of deliberately introducing nucleic acids into eukaryotic cells. Variations may be present for the vector or reagent delivered or the method of transfection across a cell or nuclear membrane. A number of variations are included in this single cell transfection chip system 100.

In an example, the single cell transfection chip system 100 may include a cell source 102 that provides cells to a fluidic channel 104 mounted on the transfection chip 106. In various examples, the cell source 102 is a refillable reservoir built into transfection chip 106, as discussed further with respect to FIG. 2. The cells may be eukaryotic cells that can have diameters in the range of 10-100 μm, or prokaryotic cells that have diameters in the range of 0.1-5.0 μm. Cells with sizes outside of these ranges are also contemplated for possible use in this single cell transfection chip system 100.

In some examples, the cell source 102 is a compartment that is physically separate from the transfection chip 106. The cell source 102 contains a plurality of cells that are to be transfected. In one example, the cell source 102 is connected to the fluidic channel with a flow control connection such that a supply of cells may be enabled or disabled based on the rate cells are flowing from the cell source to the fluidic channel 104.

The fluidic channel 104 is physically constructed on the transfection chip 106 and may be sized so that only one cell may travel through the fluidic channel 104 at a time. This may be performed using an inner diameter that is the size of a eukaryotic cell. In an example, the inner diameter of a fluidic channel is between 10 and 150 μm. In another example, the inner diameter of a fluidic channel is between 0.1-5.0 μm. The smaller inner diameter would limit not only the number of cells that could pass through the channel but also the type of cells. In an example, the fluidic channel 104 is any form of microfluidic channel.

The transfection chip 106 may be a physical construction that may include any number of the following components: a circuit board; a printed circuit board; a wafer; a silicon chip; plastic; or other suitable materials. The transfection chip 106 may include control components. The transfection chip 106 can act as a common physical connection surface for many of the components used in the transfection process. The transfection chip 106 may be the physical mount for a number of elements for single cell transfection. Some of these elements include the transfection chip 106, a reagent receiver 108 that is receiving reagents from a reagents dispenser 110, and the transfection chamber 112. The reagent dispenser 110 is physically separate from the transfection chip 106 and instead connects to a reagent receiver 108 that is mounted on the transfection chip 106.

The reagent dispenser 110 may dispense reagent which is a substance suitable for the transfection attempt. In some examples, the reagent dispenser 110 is a refillable reservoir that is constructed into the transfection chip 106. The reagent may be a chemical to induce chemical transfection, such as lipofection using lipofection agents. In another example, the reagent dispenser may dispense nucleic acid sequences in a solution that, once inside the transfection chamber 112, enables transfection of a desired vector into the single cell. As used herein, the term vector refers to a genetic vector, which is a vehicle for delivering DNA into a cell. A vector can be a DNA plasmid, a virus, or an artificial chromosome.

In some examples, the transfection chamber 112 is an electrotransfection chamber that uses electroporation elements to induce transfection. In these examples, the transfection chamber 112 may include a single or multiple electroporation elements inside the transfection chamber 112, surrounding the outside of the volume where a cell is to be transfected. The transfection chamber 112 may also be physically mounted directly onto the transfection chip 106 as the fluidic channel 104 and reagents receiver also may be directly mounted onto the transfection chip 106.

In various examples, the transfection chamber 112 operates through constriction that may induce poration of the membrane of a cell. A constricting design shrinks the size of the channel to a size small enough so that the edges of the chamber exert physical pressure on the cell within transfection chamber 112. This increased constriction pressure results in sufficient poration of the cell membrane to enable transfection.

Figure 3:
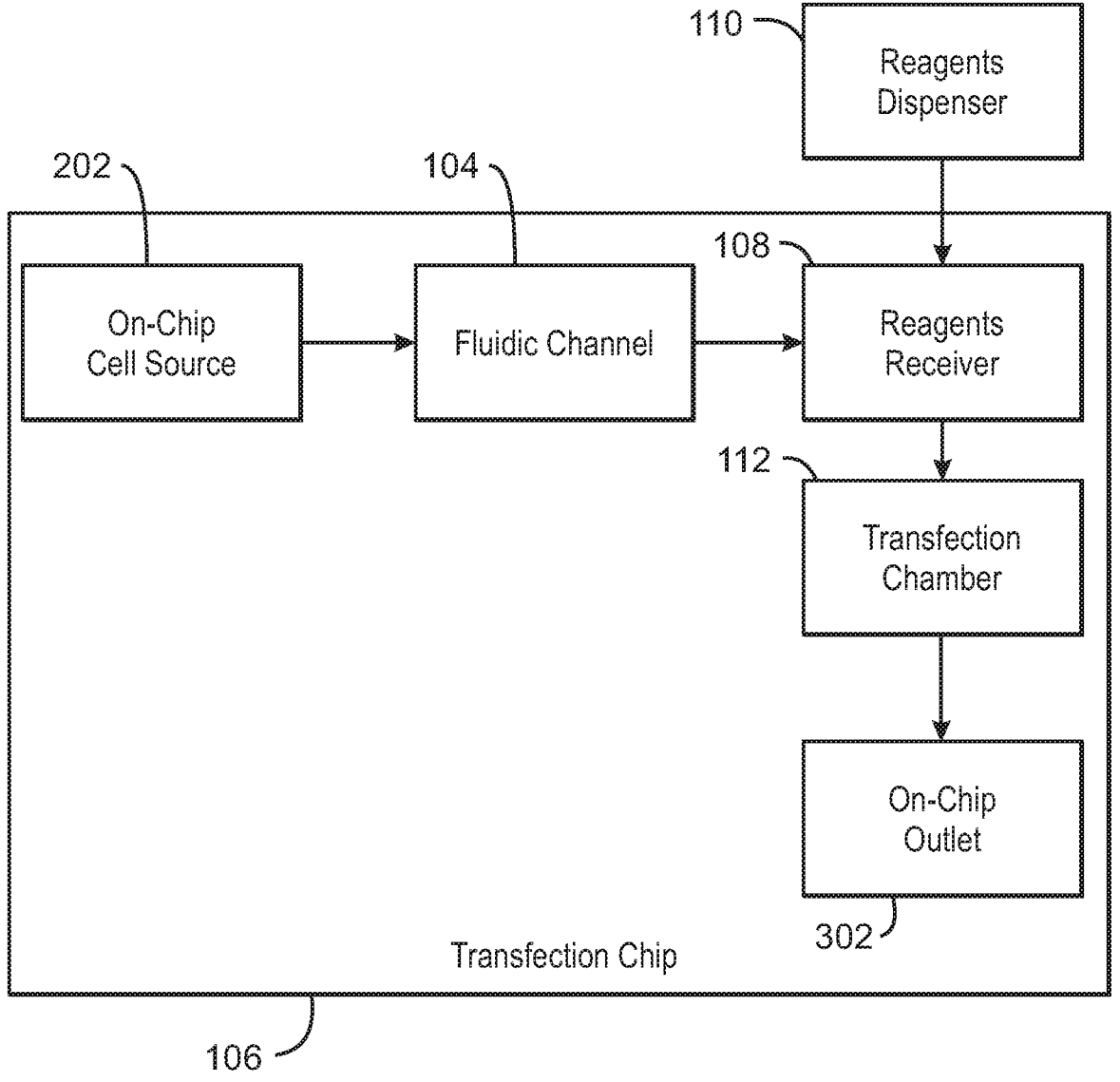
FIG. 3 is a block diagram of a single cell transfection chip with an on-chip cell source and outlet, in accordance with an example.

Once the reagent has been transfected into the cell in the transfection chamber 112, the cell may leave the transfection chip 106 through an outlet 114. The outlet in FIG. 1 is shown separate from the transfection chip 106, as the outlet may be part of an outlet structure that is physically connected to the transfection chamber 112 but not physically connected to the transfection chip 106. By contrast, the outlet shown in FIG. 3 is part of a structure that is physically connected to both the transfection chamber 112 and the transfection chip 106. In an example, a number of transfection chambers 112 are disposed in a serial chain between the first transfection chamber 112 and the outlet 114. This serial arrangement could be to enable transfection with multiple reagents. In an example, there is a second reagent receiver located between a first and a second transfection chamber so that cell may be transfected with two different reagents delivered in a specific sequence. In an example, each additional reagent receiver and transfection chamber is located physically on-chip.

Figure 2:
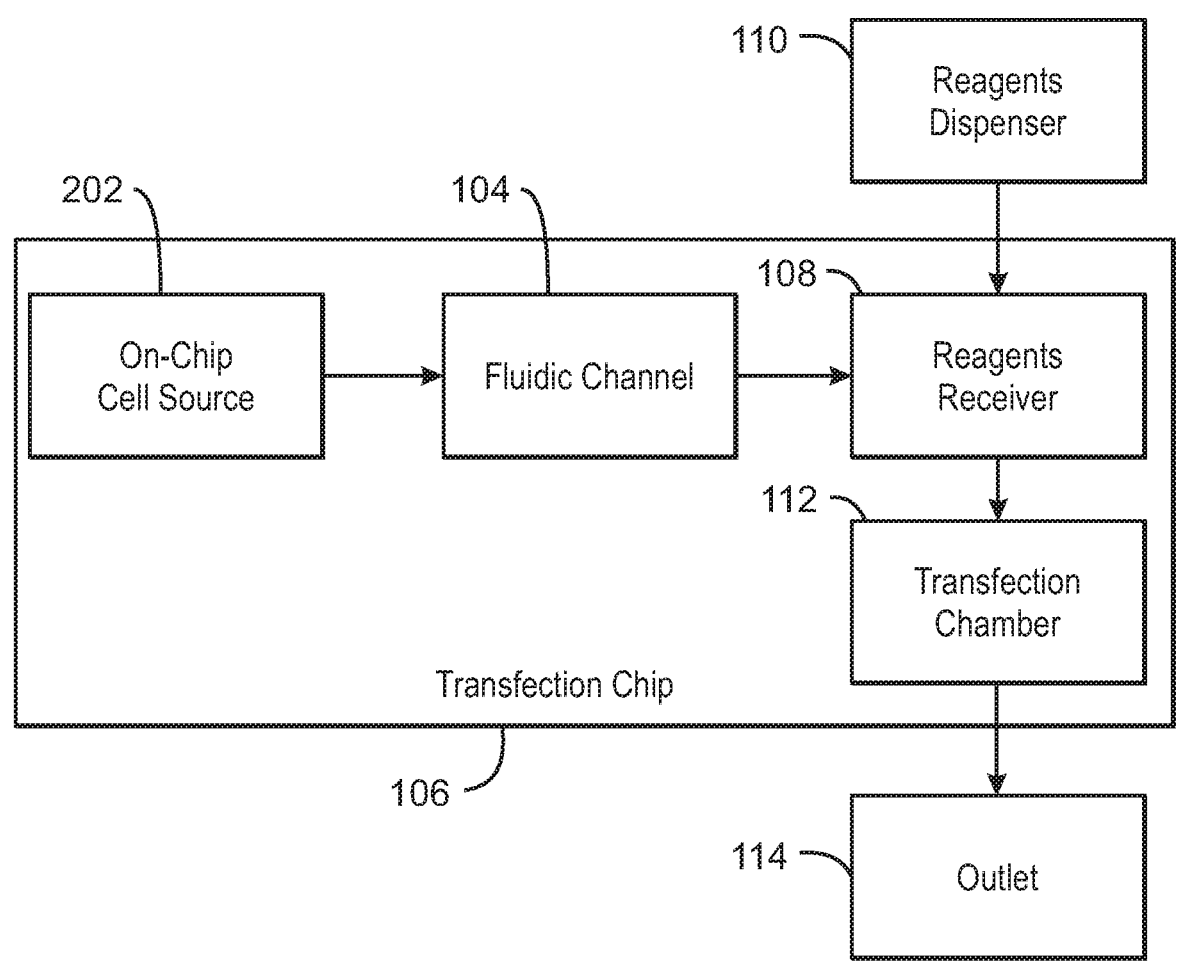
FIG. 2 is a block diagram of a single cell transfection chip with an on-chip cell source, in accordance with an example.

FIG. 2 is a block diagram of a single cell transfection chip with an on-chip cell source 200, in accordance with an example. Like numbered items are as disclosed with respect to FIG. 1. The on-chip cell source 202 in FIG. 2 is physically attached to the transfection chip 106. An on-chip cell source 202 may decrease the interchangeability of cells a transfection chip 106 can handle, but may also increase precision in single cell delivery. The control of an on-chip cell source 202 would be integrated with the fluidic channel at a manufacturing level which could physically allow for tighter tolerances and electronically ensure interoperability with other components on the transfection chip 106.

FIG. 3 is a block diagram of a single cell transfection chip with an on-chip cell source and outlet 300, in accordance with an example. Like numbered items are as disclosed with respect to FIGS. 2 and 3. The on-chip outlet 302 in FIG. 3 is physically attached to the transfection chip 106 without the transfection chamber 112 acting as the sole connection to the outlet. In an example, the on-chip outlet 302 is an opening connected by a fluid flow channel to the transfection chamber that outlets the transfected cell by gravity or by the fluid pressure of reagent and cells being pumped from upstream of the transfection chamber 112. In an example, the on-chip outlet 302 includes electronics such as a micro-fluidic ejector that may jet a transfected cell out of an opening in the on-chip outlet 302. In an example, the on-chip outlet 302 enables increased electronic connection to enable an ejecting or pump system in the on-chip outlet 302. In an example, the physical connection of the on-chip outlet 302 to the transfection chip 106 increases the stability and precision of the on-chip outlet 302 when kinetically dispensing a transfected cell towards a target area, receptacle, culture, or well.

Figure 4:
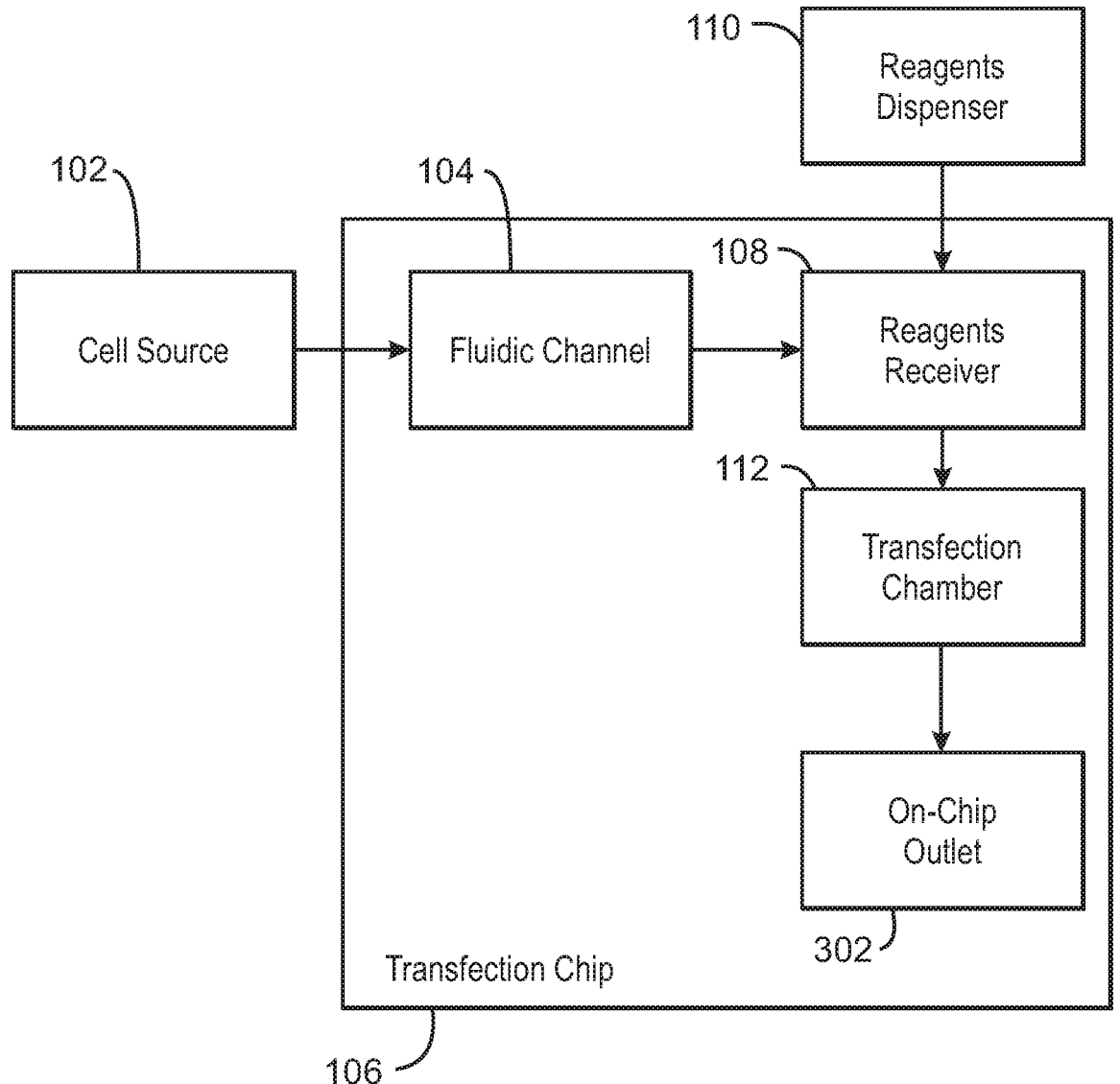
FIG. 4 is a block diagram of a single cell transfection chip with an on-chip outlet, in accordance with an example.

FIG. 4 is a block diagram of a single cell transfection chip with an on-chip outlet 400, in accordance with an example. Like numbered items are as disclosed with respect to FIGS. 1 and 3. In this figure, the transfection chip 106 is attached to an on-chip outlet 302 and not directly attached to the cell source 102 or the reagent dispenser 110. Enabling off chip cell source and reagent dispenser increases the interoperability of the transfection chip 106 with a number of different cells coming from varied cell sources and interchangeable reagents. For example, for one cell source, a first reagent may be desirable to transfect into the cell, while another cell may be transfected with a different reagent without needing to have a completely separate transfection chip 106, transfection chamber 112, and other transfection chip components.

Figure 5:
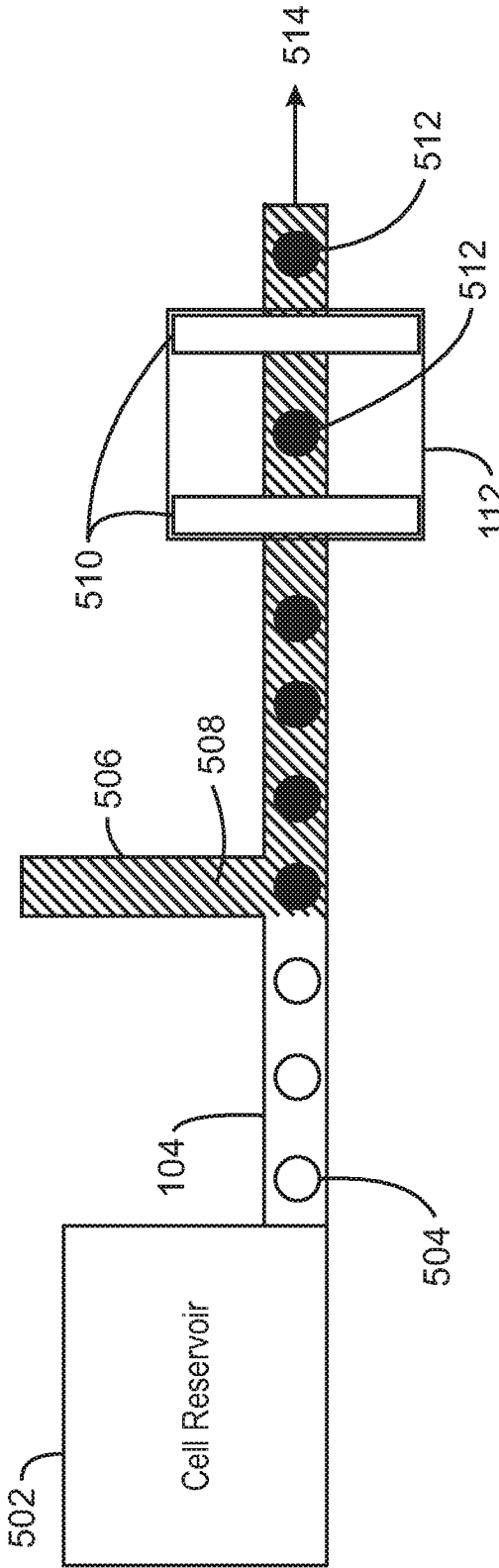
FIG. 5 is a block diagram of a single cell transfection system with a reagent receiver located upstream of the transfection chamber, in accordance with an example.

FIG. 5 is a block diagram of a single cell transfection system with a reagent receiver located upstream of the transfection chamber 500, in accordance with an example. Like numbered items are as disclosed in FIG. 1.

The cell reservoir 502 and fluidic channel 104 can deliver cells 504 to the transfection section inside the transfection chamber 112. As used herein, the cell reservoir can include both an on-chip cell source 202 and cell source 102 that is not located on the transfection chip 106. The reagent receiver 506 may intersect with the fluidic channel upstream of the transfection chamber 112. In an example, the fluid flow direction from a cell reservoir 502 is towards the transfection chamber 112. The fluid flow from the reagent receiver 506 includes the reagent 508 which once intersected with the fluidic channel 104 can interact with the cells 504. The interaction of the reagent 508 with the cell 504 can include applying staining to the cell, a genetic vector to be transfected into the cell, or other interactions that may take time to occur, such as physical binding. In an example, the location at which the reagent receiver 506 intersects with the fluidic channel is based on how long a reagent is intended to interact with the cell 504 prior to entering the transfection chamber 112. In an example, the reagent receiver 506 intersects with the fluidic channel 104 based on a cell movement rate and the time needed for the reagent to interact with the cell 504 prior to the transfection chamber 112.

The reagent receiver 506 may receive reagent from a reagent dispenser that delivers on-demand transfection material for either a single cell, a portion of cells from a cell reservoir, or a group of distinct cells provided by the cell reservoir interchanging the cell source. In an example, there is one reagent dispenser.

The transfection chamber 112 may include electroporation elements 510 for enhancing staining of inside of cell 504, or electrotransfection of the cell 504. Once a cell 504 has been transfected is becomes a transfected cell 512 and exits the transfection chamber 112. The transfected cell 512 may exit the outlet 514. In an example, the outlet 514 is either an orifice or a directed channel towards another transfection chamber or reagent receiver complex. In an example, the outlet 514 also includes an ejector to eject cells onto specific portions of a chip such as a multiwell plate for further cell analysis. In an example the outlet ejects the cells into a collection reservoir so that further processes may be applied to the cells on the transfection chip.

Figure 6:
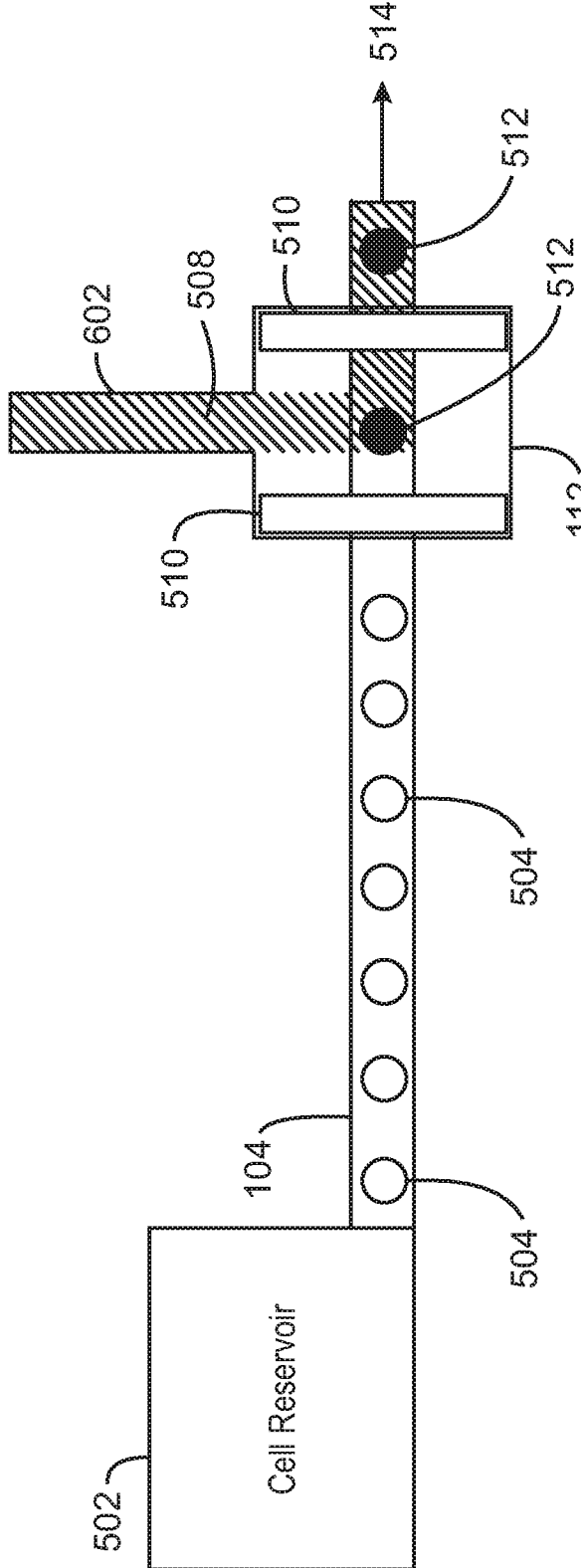
FIG. 6 is a block diagram of a single cell transfection system with a reagent receiver connected to the transfection chamber, in accordance with an example.

FIG. 6 is a block diagram of a single cell transfection system with a reagent receiver connected to the transfection chamber 600, in accordance with an example. Like numbered items are as disclosed with respect to FIGS. 1 and 5. The reagent receiver 602 now inserts reagent directly into the transfection chamber 112 rather than upstream of the transfection chamber 512 in the fluidic channel 104. This type of reagent insertion via the reagent receiver 602 reduces the interaction time between the reagent 508 and the cell 504 prior to transfection in the transfection chamber 112.

Figure 7:
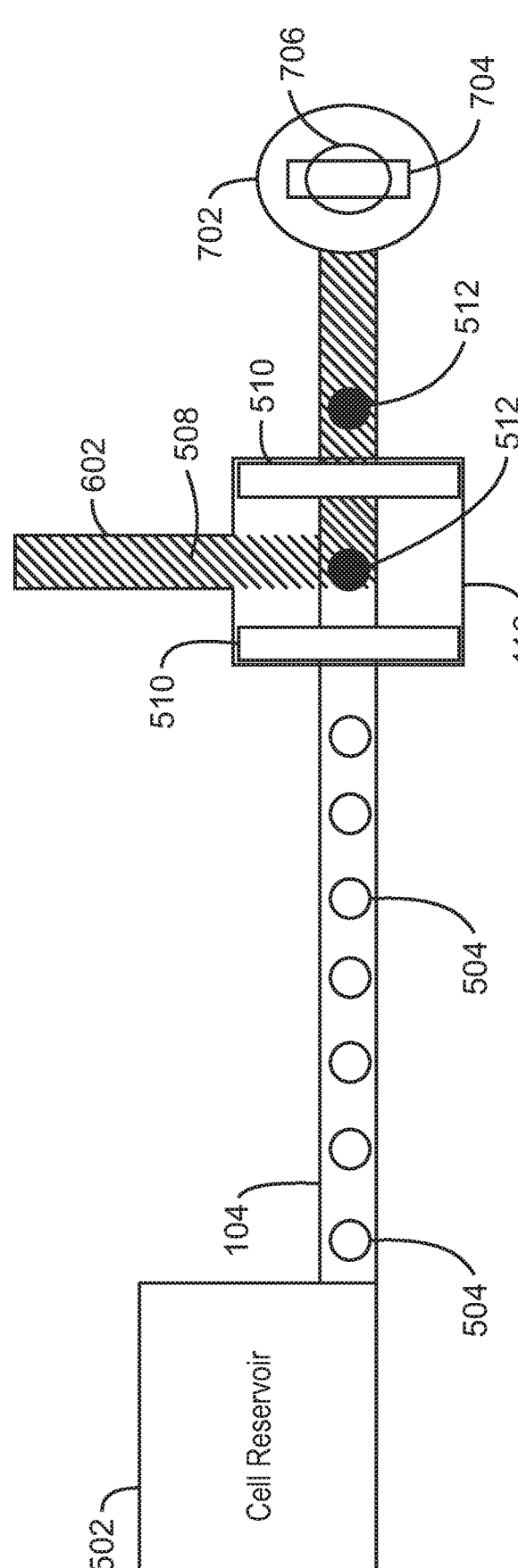
FIG. 7 is a block diagram of a single cell transfection system with a microfluidic ejector and drop ejector orifice, in accordance with an example.

FIG. 7 is a block diagram of a single cell transfection system with a microfluidic ejector and drop ejector orifice 700, in accordance with an example. Like numbered items are as disclosed with respect to FIGS. 1, 5, and 6.

Downstream of the transfection chamber 112 may be a microfluidic ejection chamber 702. The transfection chamber may connect to the microfluidic ejection chamber through an outlet. The microfluidic ejection chamber 702 can include a microfluidic ejector 704 and a drop ejector orifice 706. In an example, the microfluidic ejector 704 can be a thin-film resistors capable of producing sufficient heat to fire a droplet containing the transfected cell 512 through the drop ejector orifice 706. The microfluidic ejection chamber and microfluidic ejector may include or have similar technical specifications and design as a thermal inkjet chamber and thermal inkjet resistor, respectively. Likewise, the microfluidic ejection chamber and microfluidic ejector may instead have similar technical specifications and design as a piezoelectric chamber and piezoelectric element, respectively. To eject a droplet out of the microfluidic ejection chamber 702 a pulse of current can be passed through the microfluidic ejector 704 to cause a rapid vaporization of the fluid carrying the transfected cell 512 in order to form a bubble; the bubble causing a large pressure increase and propelling a droplet containing the transfected cell out of the drop ejector orifice 706.

The mechanism of the microfluidic ejection chamber may also aid in moving the fluid into the transfection chamber 112 from the fluidic channel 104, cell reservoir 502, and reagent receiver 602. Specifically, the pulling tension of the fluid carrying the cell 504 and later the transfected cell 504 combined with the resultant contraction of the vapor bubble after the firing of the microfluidic ejector 704 pulls fluid and a cell 504 into the transfection chamber 112. In an example, the fluid is water. Another mechanism for movement of the fluid through the fluidic channel 104 towards the transfection chamber 112 is an inertial pump using microfluidic ejectors located inside the fluidic channel 104. In an example, another mechanism for movement of the fluid through the fluidic channel 104 towards the transfection chamber 112 is a T-pump including a microfluidic ejector located in a pocket connecting to but out of the direct path of the fluidic channel 104.

Figure 8:
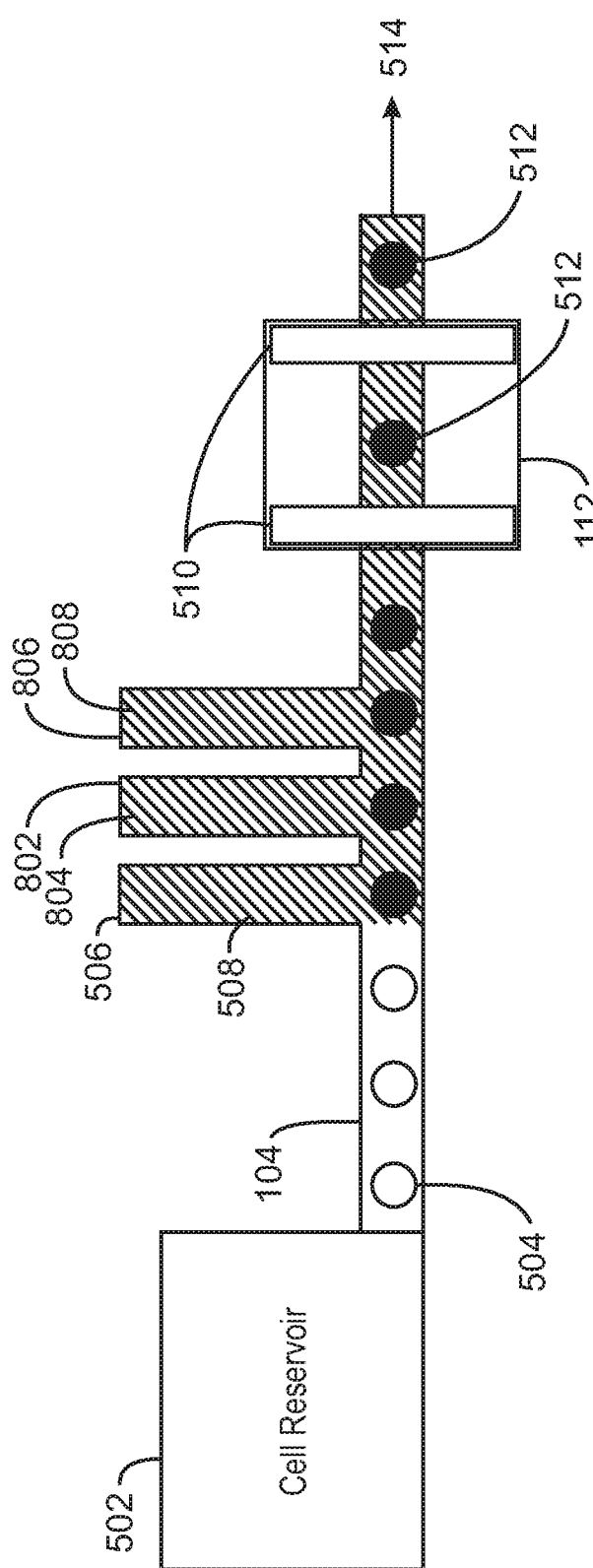
FIG. 8 is a block diagram of a single cell transfection system with multiple reagent receivers, in accordance with an example.

FIG. 8 is a block diagram of a single cell transfection system with multiple reagent receivers 800, in accordance with an example. Like numbered items are as disclosed with respect to FIGS. 1 and 5.

In addition to a first reagent receiver 506 dispensing a first reagent 508 upon intersection with the fluidic channel 104, the system shown includes a number of additional reagent receivers. A second reagent receiver 802 carrying a second reagent 804 and a third reagent receiver 806 is shown carrying a third reagent 808 towards the transfection chamber 112 via the fluidic channel 104.

The ability to insert multiple interchangeable reagents into the system upstream of the transfection chamber enables a large number of combinatorial applications. For example, a number of cells may be transfected with a first reagent, another number of cells transfected with a first and second reagent, another group of cells transfected with a first, second, and third reagent, another group of cells transfected with a second and third reagent, another group of cells transfected with the second reagent, another group of cells transfected with the third reagent. By enabling a larger number of reagent receivers to intersect with the fluidic channel, the system enables a large combination of either cell markers or genetic vectors or a combination of these reagents to be applied to cells prior to transfection. In an example, the distance of reagent receivers varies depending on the reagent they carry and the time intended for each reagent to interact with the cell 504 prior to transfection in the transfection chamber 112. In an example, a first reagent receiver 506 intersects with the fluidic channel 104 prior to, or upstream of, the transfection chamber. In this example, a second reagent receiver 802 may not intersect with the fluidic channel 104 prior to the transfection chamber 112 instead releasing the second reagent 804 directly into the transfection chamber 112.

In an example, the reagents can be any combination of transfecting materials, stains, or cell interacting reagents. For example, multiple transfecting materials, e.g. genetic material, may correspond to each of the number of reagent receivers shown thereby enabling multiple transfecting reagents are present in the transfection chamber at once without needing to mix the transfecting agents prior to dispensing. The distribution of multiple transfection materials may be, as disclosed above, done in a combinatorial manner.

Figure 9:
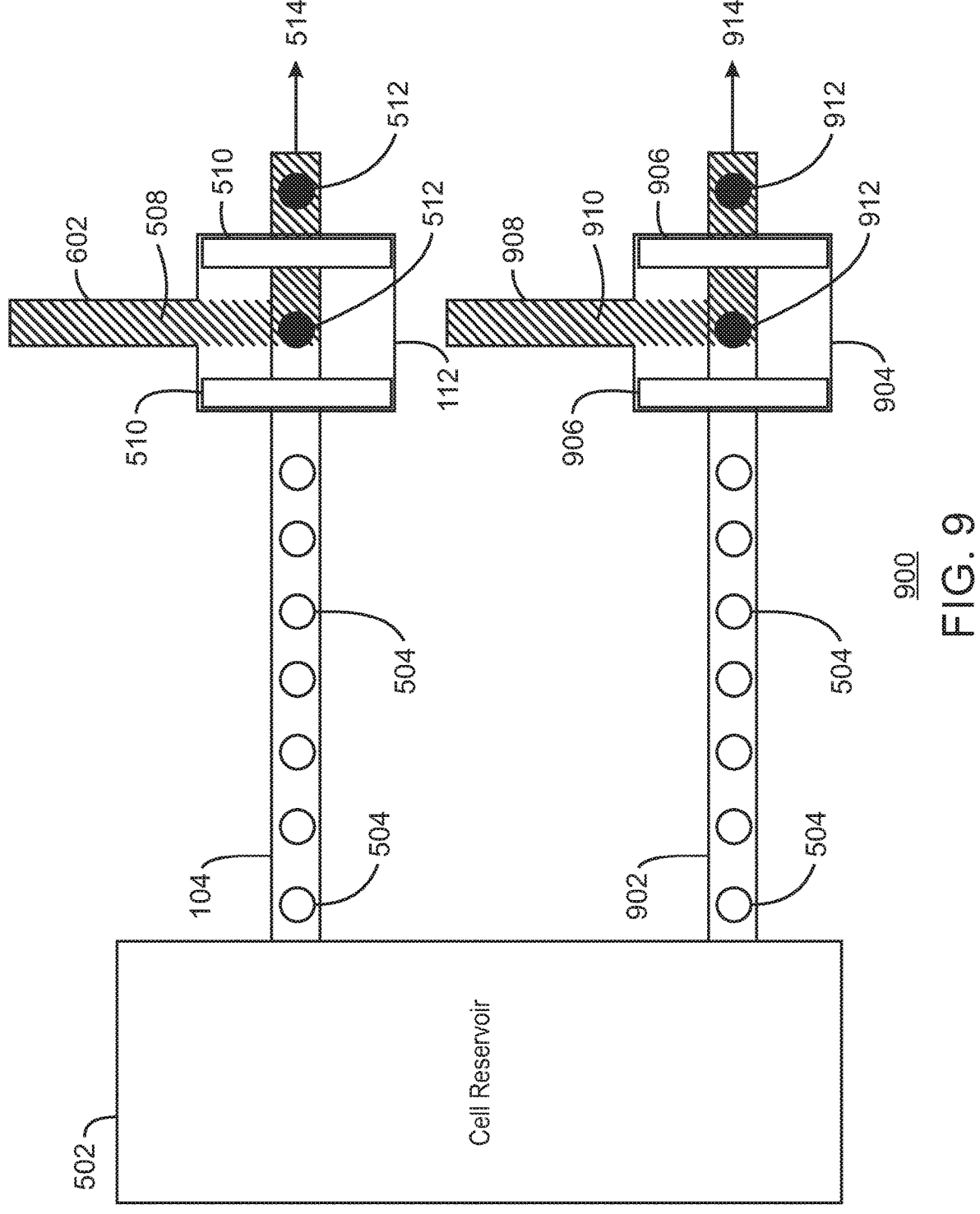
FIG. 9 is a block diagram of a single cell transfection system with parallel transfection chambers, in accordance with an example.

FIG. 9 is a block diagram of a single cell transfection system with parallel transfection chambers 900, in accordance with an example. Like numbered items are as described in FIGS. 1, 5, and 6.

The second fluidic channel 902 runs parallel to the fluidic channel 104 in that it connects to the same cell reservoir 502 however it has a separate set of components for transfection. Specifically, the second fluidic channel 902 can include a second transfection chamber 904 including separate electroporation elements 906 and a second reagent receiver 908 with a second reagent 910 input into the second transfection chamber 904. In an example, the outlet 514 of the transfection chamber 112 dispenses the transfected cell 512 into the second reagent receiver 908 in order to affect transfection of the cells in the second transfection chamber 904 or to combine and streamline fluid flow in the overall system. The parallel system also can include a second set of transfected cells 912 that are transfected with the reagent received in the second reagent receiver 908. The second transfected cell 912 may be output by the second outlet 914. In an example both the outlet 514 and the second outlet 914 combine and output to the same reservoir or may be connected to the same microfluidic ejection outlet. The outlets may also lead to further reagent receivers or transfection chambers either in parallel or in serial in any possible combination.

Figure 10:
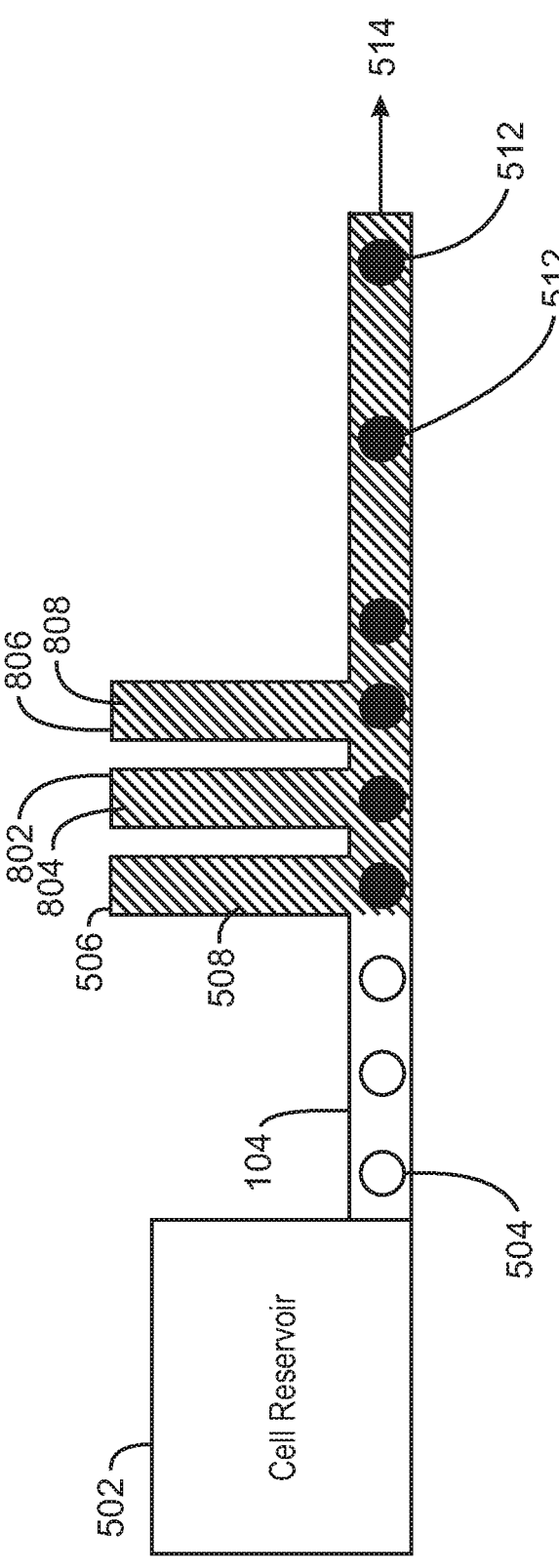
FIG. 10 is a block diagram of a single cell transfection system using chemical transfection and no separate transfection chamber, in accordance with an example.

FIG. 10 is a block diagram of a single cell transfection system using chemical transfection and no separate transfection chamber 1000, in accordance with an example. Like numbered items are as disclosed with respect to FIGS. 1, 5, and 8. A system with no separate transfection chamber may be used for chemical transfection. In an example, a chemical transfection agent is dispensed from one of the reagent receivers that connects to the fluidic channel 104. The chemical transfection may occur due to the reagent or reagents dispensed from one reagent receiver or a number of reagent receivers. In an example, one or multiple of the reagent receivers dispenses a virus for performing multiplexed viral transfection on the cells 504 in the fluidic channel 104. In an example, the outlet 514 is a microfluidic ejection chamber as described above with respect to FIG. 7.

Figure 11:
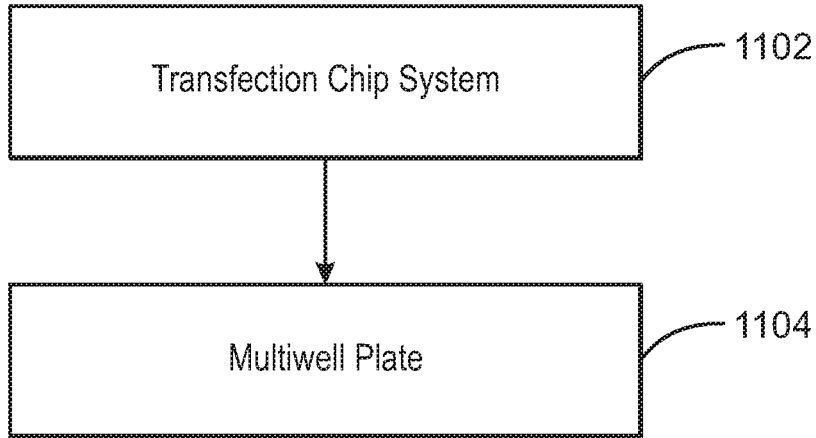
FIG. 11 is a block diagram of a single cell transfection system outputting to a multiwall plate, in accordance with an example.

FIG. 11 is a block diagram of a single cell transfection system outputting to a multiwall plate 1100, in accordance with an example. The transfection chip system 1102 can include any of the systems shown in FIG. 1-10. The output of the transfection chip system 1102 may be a transfected cell into a multiwall plate 1104 for further analysis. The nature of the fluidic chambers described above being able to limit transfection to a single cell at a time enables dispensing of a single transfected cell at a time each into a separate well of a multiwall plate for separate observation an analysis. In an example, the multiwall plate 1104 can be any ejection medium used for further analysis or manipulation including a reservoir for collecting transfected cells for use as a batch or ejection onto a specified location on a medium such as a growth medium or culture. Both the transfection chip system 1102 and the multiwall plate 1104 may be located within an incubator system or removably and/or robotically placed in an incubator in order to fully automate transfection and cell growth in a single system or device.

Figure 12:
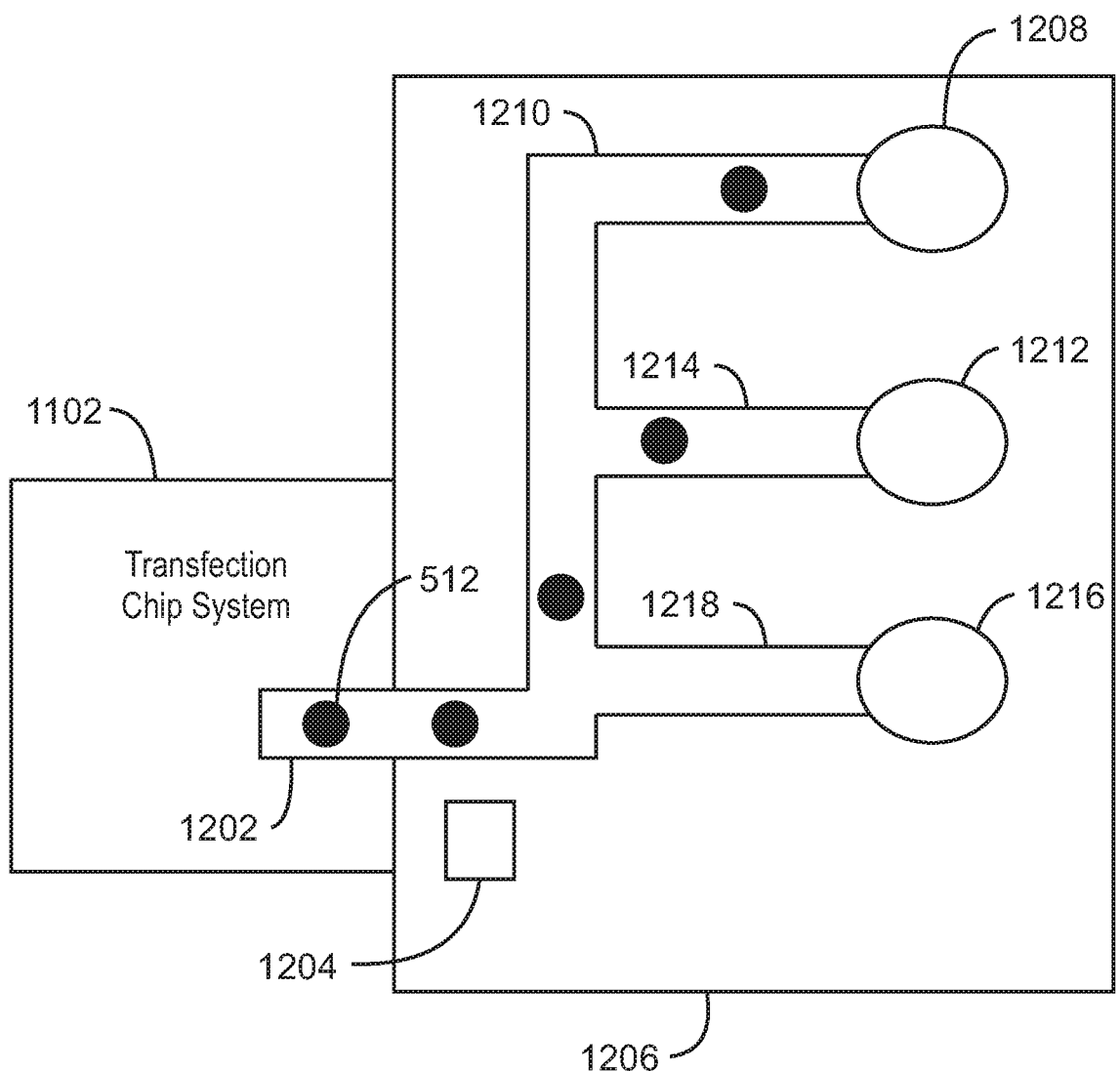
FIG. 12 is a block diagram of a single cell transfection system with a cell analyzing sorter using microfluidic ejectors, in accordance with an example.

FIG. 12 is a block diagram of a single cell transfection system with a cell analyzing sorter using microfluidic ejectors 1200, in accordance with an example. Like numbered items are as described in FIGS. 5 and 11.

The transfected cell 512 may travel through a bridging channel 120 to move the transfected cell 512 from the transfection chip system 1102. The bridging channel may expose the transfected cell 512 to a cell analyzer 1204 within a sorting system 1206. The cell analyzer may detect a characteristic of the transfected cell using optical analysis to detect a dye or stain on the transfected cell. Other cell analysis may be conducted by the cell analyzer that could identify the physical, chemical, or other characteristics of the transfected cell 512 as it passes through the bridging channel 120.

Based on a detected characteristic of the transfected cell as detected by the cell analyzer, the sorting system may activate a first jetting resistor in a first microfluidic ejection chamber 1208 thereby directing the transfected cell 512 towards the first outlet channel 1210. As discussed above with respect to FIG. 7, in response to jetting action undertaken by a jetting chamber such as the first jetting chamber 1208, the tension and collapsing vapor bubble may pull upstream fluid towards it. In a system with multiple channels and jetting chambers, activating a certain chamber will cause fluid flow towards that particular chamber and channel.

As further example, if a second characteristic is detected by the cell analyzer 1204 the second jetting chamber 1212 may activate a second jetting resistor it contains. The second jetting resistor may jet fluid and through the collapse of the bubble formed by the jetting process, the transfect cell 512 can be pulled towards the second outlet channel 1214 as fluid moves to fill the space created by the jetting action. Similarly, a third characteristic detected by the cell analyzer 1204 of a transfected cell 512 could signal for the sorting system 1206 to activate the third jetting chamber 1216 and pull the transfected cell 512 into the third outlet channel 1218.

Figure 13:
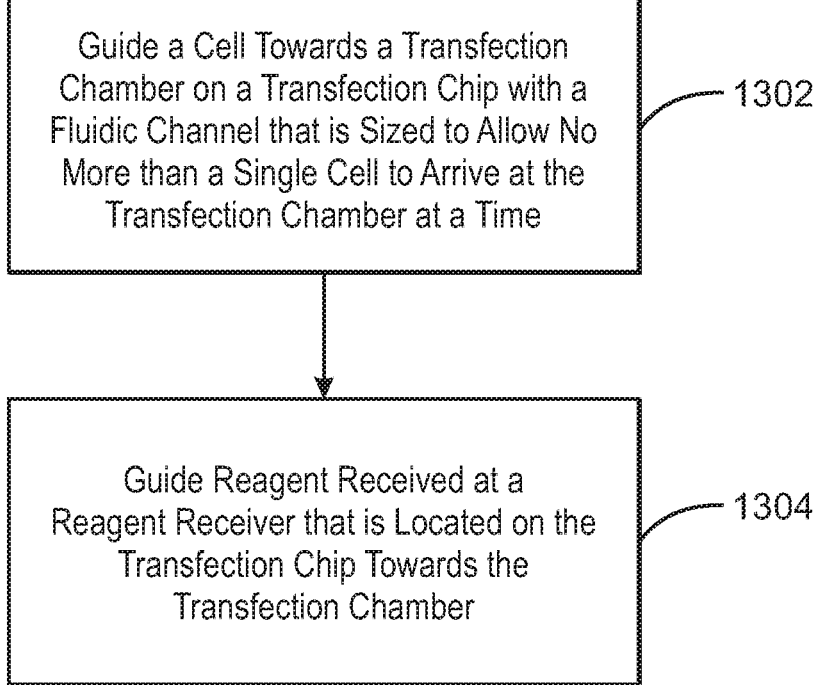
FIG. 13 is a flowchart of a method for single cell transfection, in accordance with an example.

FIG. 13 is a flowchart of a method 1300 for single cell transfection, in accordance with an example. At block 1302, the method 1300 includes guiding a cell towards a transfection chamber on a transfection chip with a fluidic channel that is sized to allow no more than a single cell to arrive at the transfection chamber at a time.

At block 1304, the method 1304 includes guiding a reagent received at a reagent receiver that is located on the transfection chip towards the transfection chamber, the reagent receiver to intersect with the path of the fluidic channel. In an example, the reagent receiver intersects with the path of the fluidic channel prior to or upstream of the transfection chamber. In another example, the reagent receiver intersects with the path of the fluidic channel at the transfection chamber.

Other variations of this method 1300 include a method that performs single cell transfection that includes microfluidic ejector located on the transfection chip, the microfluidic ejector to jet a transfected cell through a drop ejector orifice in the transfection chip. In an example, the method 1300 performing single cell transfection includes a second reagent receiver located on the transfection chip guiding a second received reagent towards the transfection chamber and intersecting with the path of the fluidic channel prior to the transfection chamber. In an example, the method 1300 performing single cell transfection may include a second transfection chamber in the path between the transfection chamber and an outlet of the transfection chip.

Another example could include in the method use of a second transfection chamber on the transfection chip with a second fluidic channel located on the transfection chip guiding a cell towards the second transfection chamber. In this example, the second fluidic channel could be sized to allow no more than a single cell to arrive at the second transfection chamber at a time, the fluidic channel and the second fluidic channel to connect to the cell reservoir.

In another example for implementing the method 1300, a first microfluidic ejector could be located along a first outlet channel, the first microfluidic ejector to jet fluid out of a first outlet. In this example, a second microfluidic ejector along a second outlet channel may jet fluid out of a second outlet. Furthermore, the method could make use of a cell analyzer to detect a characteristic of a cell output from the transfection chamber, the cell analyzer to signal for the activation of either the first microfluidic ejector or the second microfluidic ejector based on the characteristic detected. In another example, the transfection chamber is a designated length of the fluidic channel downstream of a point of intersection between the reagent receiver and the fluidic channel, wherein the designated length is based on the amount of time for a reagent received in the reagent receiver to enable chemical transfection in a cell after the reagent enters the fluidic channel.

While the present techniques may be susceptible to various modifications and alternative forms, the techniques discussed above have been shown by way of example. It is to be understood that the technique is not intended to be limited to the particular examples disclosed herein. Indeed, the present techniques include all alternatives, modifications, and equivalents falling within the scope of the following claims.

What is claimed is:

1. A system for single cell transfection comprising:

a transfection chamber on a transfection chip;

a fluidic channel located on the transfection chip for guiding a cell towards the transfection chamber, the fluidic channel sized to allow no more than a single cell to travel from a cell reservoir through the fluidic channel to arrive at the transfection chamber at a time;

a microfluidic ejector;

a first reagent receiver located on the transfection chip guiding a first received reagent towards the transfection chamber and intersecting with a path of the fluidic channel upstream of the transfection chamber; and a second reagent receiver located on the transfection chip guiding a second received reagent towards the transfection chamber and intersecting with the path of the fluidic channel upstream of the transfection chamber, wherein the first reagent receiver intersects the fluidic channel at a first distance from the transfection chamber and the second reagent receiver intersects the fluidic channel at a second distance from the transfection chamber different from the first distance, wherein the transfection chamber comprises a constriction reducing a size of the fluidic channel such that edges of the transfection chamber apply a physical pressure on the cell within the transfection chamber, the physical pressure to porate a cell membrane of the cell to receive the first reagent from the first reagent receiver;

wherein the transfection chamber comprises a first electroporation element inside the transfection chamber on a first edge of the edges of the transfection chamber, the first edge configured to receive the cell from the fluidic channel, and a second electroporation element inside the transfection chamber on a second edge of the edges of the transfection chamber opposite the first edge of the transfection chamber, the second edge configured to output the cell to the microfluidic ejector.

2. The system of claim 1 further comprising a microfluidic ejection chamber comprising the microfluidic ejector located on the transfection chip to eject a transfected cell, the microfluidic ejector aligned with a drop ejector orifice in the microfluidic ejection chamber.

3. The system of claim 1 further comprising a second transfection chamber in a path between the transfection chamber on the chip and an outlet of the transfection chip.

4. The system of claim 1 further comprising:

a second transfection chamber on the transfection chip; and a second fluidic channel located on the transfection chip guiding a cell towards the second transfection chamber, the second fluidic channel sized to allow no more than a single cell to arrive at the second transfection chamber at a time, the fluidic channel and the second fluidic channel to connect to a cell reservoir.

5. The system of claim 1, wherein the microfluidic ejector is:

a first microfluidic ejector along a first outlet channel to jet fluid out of a first outlet;

and the system further comprises a second microfluidic ejector along a second outlet channel to jet fluid out of a second outlet; and a cell analyzer configured to detect a characteristic of a cell output from the transfection chamber, the cell analyzer configured to signal activation of either the first microfluidic ejector or the second microfluidic ejector based on the characteristic detected.

6. The system of claim 1, wherein the constriction is within the transfection chamber.

* * * * *